US00PP26571P3

(12) United States Plant Patent
Acosta

(10) Patent No.: US PP26,571 P3
(45) Date of Patent: Apr. 5, 2016

(54) AVOCADO TREE NAMED 'NICO'

(50) Latin Name: *Persea americana mille*
Varietal Denomination: Nico

(71) Applicant: Acosta Farms, Inc., Miami, FL (US)

(72) Inventor: Alcides Acosta, Coral Gables, FL (US)

( * ) Notice: Subject to any disclaimer, the term of this patent is extended or adjusted under 35 U.S.C. 154(b) by 11 days.

(21) Appl. No.: 13/998,090

(22) Filed: Sep. 30, 2013

(65) Prior Publication Data

US 2015/0096085 P1 Apr. 2, 2015

(51) Int. Cl.
*A01H 5/08* (2006.01)

(52) U.S. Cl.
USPC ..... Plt./200
CPC ..... *A01H 5/0818* (2013.01)

(58) Field of Classification Search
USPC ..... Plt./200
See application file for complete search history.

*Primary Examiner* — Keith Robinson
(74) *Attorney, Agent, or Firm* — Michael C. Cesarano, P.A.

(57) ABSTRACT

The 'Nico' avocado is of medium size, average 16-22 ounces and being about 5.3 inches in length, and has overall good eating qualities. The fruit matures and can be picked in March to early April. The fruit is an ovate berry that has a soft shelled, smooth textured, exocarp that is dark green.

3 Drawing Sheets

Scientific name: *Persea americana mille* var. 'Nico'.

BRIEF SUMMARY OF THE INVENTION

The tree is in a 40 acre avocado grove located in Miami-Dade County, Fla. The tree is estimated to be between 20 to 25 years old. The fruit differs from other avocados because it ripens later than others. Its origin is unknown. Its fruit can be stored at temperatures above 50° Fahrenheit.

Parentage is unknown as the tree was discovered, and is of a wild nature. The tree has been observed for four years, and has been in production for 15 years. A comparison of the microsatellite pattern from this avocado against 13 known varieties ('Lula' (not patented), 'Simmonds' (not patented), 'Monroe' (U.S. Pat. No. 261), 'Choquette' (not patented), 'Semil-34' (not patented), 'Semil-43' (not patented), 'Melendez' (not patented), 'Hall' (not patented), 'Booth' (not patented), 'Hardee' (not patented), 'April' (not patented), 'Carla' (U.S. Plant Pat. No. 16,594), and 'Pollock' (not patented)) revealed no matches.

Asexual propagation was attained in 2009 in Miami-Dade County, Fla. when the plant was 20 years old. Asexual reproduction was achieved by grafting cuttings of the tree onto new avocado seedlings. The tree differs from other late varieties on the lateness of the maturity of the fruit. 'Nico' presents resistance to *Pseudocercospora purpurea* pathogens.

BRIEF DESCRIPTION OF THE DRAWINGS

FIG. 1 shows the trunk at a lower portion of the 'Nico' avocado tree.

FIG. 2 shows the midlevel portion of the 'Nico' avocado tree.

DETAILED BOTANICAL DESCRIPTION

Figure 3:
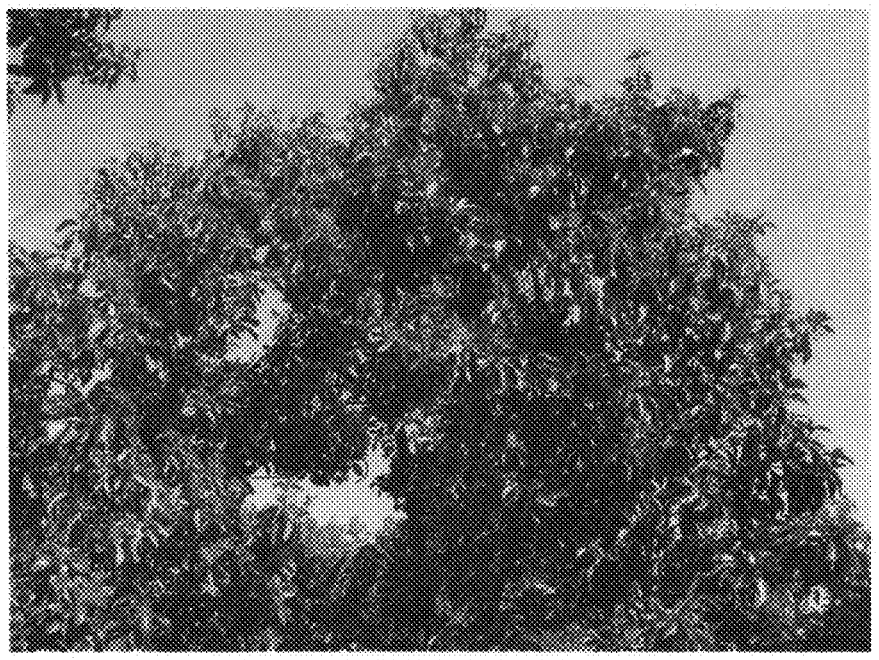
FIG. 3 shows the upper portion of the 'Nico' avocado tree.
Figure 4:
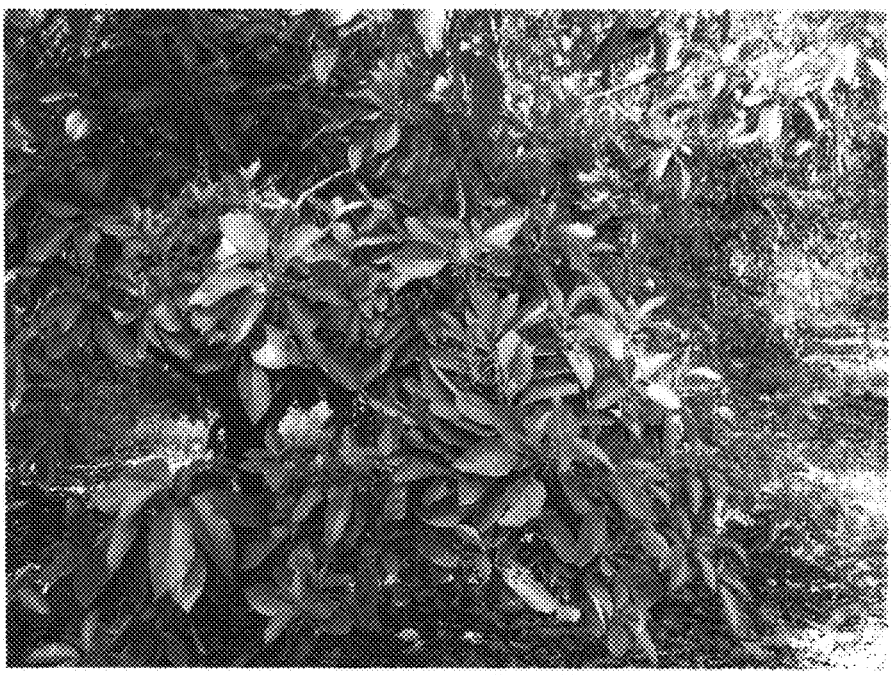
FIG. 4 shows a detailed view of the leaf of the 'Nico' avocado tree near the base.

Botanical descriptions used herein are described using *Exotica Pictorial Cyclopedia of Exotic Plants*, A. B. Graf, page 1834, "Botanical Terms Illustrated." Where possible, color is described using the HEX value designation obtained from the web site, www.cloford.com.

The tree presents a vigorous upright growth with a spread of 15' and 25' high (before pruning). As shown in FIG. 1, at a height of 2', the main trunk has a diameter of 11.5" and a circumference of 36", tapering as it extends straight and upward to the pinnacle of the tree. The main trunk splits into 4 branches of which two are main scaffold limbs of about 5.1" and 6.8" in diameter, with smaller limbs each being about 3.5" in diameter, with the vertical sub trunk splitting into smaller branches as it extends upward. Limbs range from 3-10 feet from the main axis of the tree.

The trunk is corky and rough, and the bark of the trunk is an indeterminate brown to greenish brown in color owing to a repeated copper hydroxide spray regimen. Lenticels are prominent on limbs of green wood but are obscured as bark ages and becomes corkier.

The leaves are ovate and have a smooth upper surface marked by a lighter venation that is very slightly raised, with the upper smooth surface becoming a leathery texture as they mature, as appears in FIGS. 1, 2, 3, and 4. The leaf tip is acuminate. The margin is entire and undulate. The upper leaf color is "olivedrab 3" (yellow green), HEX value #9ACD32 and the underside of the leaves are a shade lighter in color, "dark olive green 2", HEX value #BCEE68. Veins are prominently raised and the number of veins from mid-rib average 10. The length of leaf blades varies from 4.5" to 7" (11.43 cm to 17.8 cm), with the average length being 5.9" (15 cm). The width of leaf blades varies from 2.4" to 3.4" (6 cm to 7.2 cm), with the average width being 2.8" (7.1 cm). The foliage is of heavy density near the ground, becoming sparse toward the upper regions of the tree. Typical observed petiole diameter is 3.4-3.8 mm and petiole lengths range from 1-1.4" (2.5-3.6 cm), with an average length being 1.1" (2.8 cm). Internodes are between ⅜"-½" (0.95 cm to 1.27 cm), and the angle of the leaf at the point of attachment ranges from 60° to 80°.

Buds are yellow-green, have an average length of 8-9 mm, average width of 3.5 mm, and an oblong shape with a rounded base and acute tip. Pedicels are green-yellow in color and average 5-6 mm in length and 1.2 mm in width with an average diameter of 1 mm. Peduncles range from 41 mm to 151 mm and average about 85 mm and are yellow green in color. Typical observed flower depth is 7.5-8 mm.

The flowers of this plant have 3 lobes that are approximately 6.5 mm in length and 2 mm in width. Flowers typically have three sepals of about 6 mm in length and 3 mm in width. Margins are smooth and uniform, smooth in texture, and have densely silk tomentose on both surfaces. The shape is apex acute with a flattened base.

The fruit shape is ovate, averaging 4" in diameter, has a texture that is buttery, has no discernable neck, and may be distinguished over the fruit of co-pending application Ser. No. 13/998,168 in that the fruit is discernably more spherical, having a major axis of approximately 5" and a diameter of 4" whereas the fruit of co-pending application Ser. No. 13/998, 168 is more oblong, having a major axis of nearly 6" and a diameter of approximately 4". Another visible discernable difference is that the surface of the fruit has a medium gloss whereas the skin of the fruit of co-pending application Ser. No. 13/998,168 has a high gloss. Fruit of the 'Nico' tree may be harvested in March or early April, whereas the fruit of co-pending application Ser. No. 13/998,168 is ready for harvesting in late February or March.

The seed is round, weighing about 6.9 oz, depending on overall fruit size, having a diameter between 2.5 and 3", and fitting in a tight cavity. The plant produces fruit at a medium-high volume, averaging about 275-300 lbs per year.

The tree's winter hardness is 9B. Avocado shelf life is several weeks, and the fruit can be stored above 50°. The fruit naturally ripens once placed at room temperature or about 5-8 days after harvesting.

The flowers are not fragrant, and an anise aroma is not present. The tree blooms in March and the blooms are of the B type. Fruit matures and can be picked in March or early April of the following year. The fruit weights are between 16 and 22 ounces with the diameter averaging 4 inches. The fruit is full in flavor and peels easily. The seed is tight in the cavity and is 3 inches long and dark brown in color.

Figure 5:
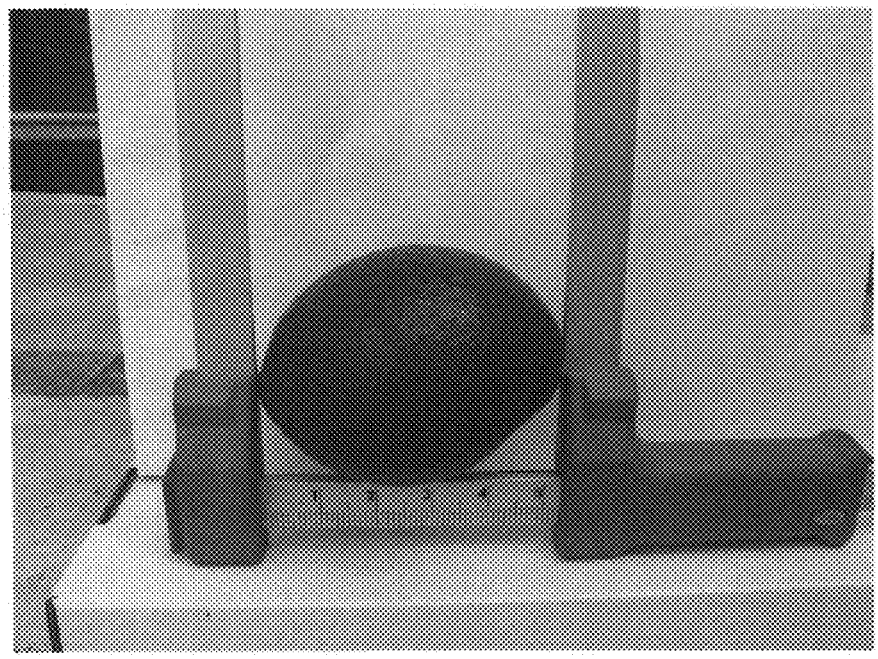
FIG. 5 shows the scale in inches of a typical fruit of the 'Nico' avocado tree measured against a ruler.

FIG. 5 shows the outside of the fruit, which is an ovate berry that matures in March. It has a thin (1/32") soft shelled exocarp, which is smooth textured, and dark green. The fruit weighs 12-16 ounces and averages 5.3" in length, as shown in FIG. 5.

Figure 6:
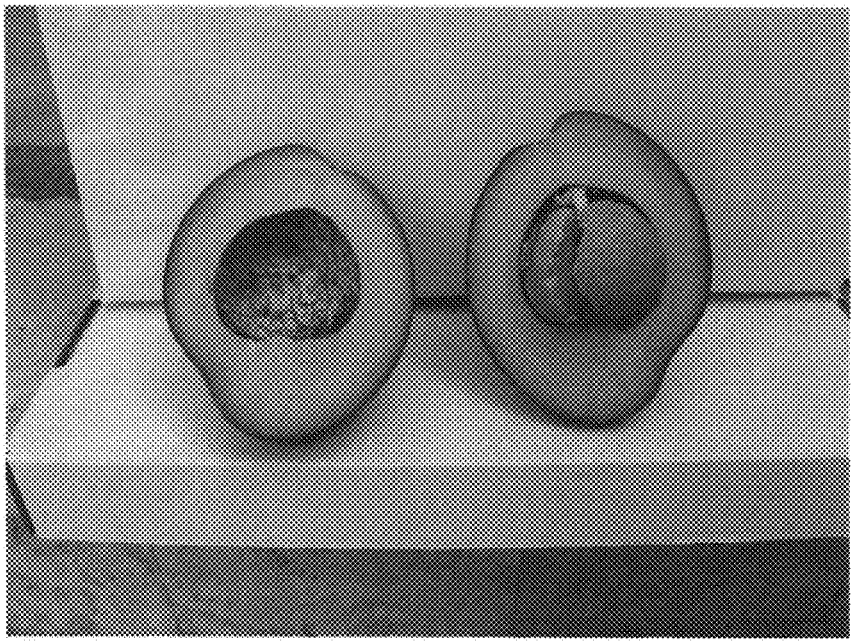
FIG. 6 shows the color and internal configuration of the fruit and the seed of the 'Nico' avocado tree.

In FIG. 6, the interior of the fruit is seen to have a mesocarp color that is green near the shell and yellow near the seed cavity.

The invention claimed is:

1. A new and distinct variety of avocado tree substantially as described and illustrated and characterized as to novelty by its overall good eating qualities, its medium size and its being ready to be picked in March to early April.

* * * * *

Fig. 1
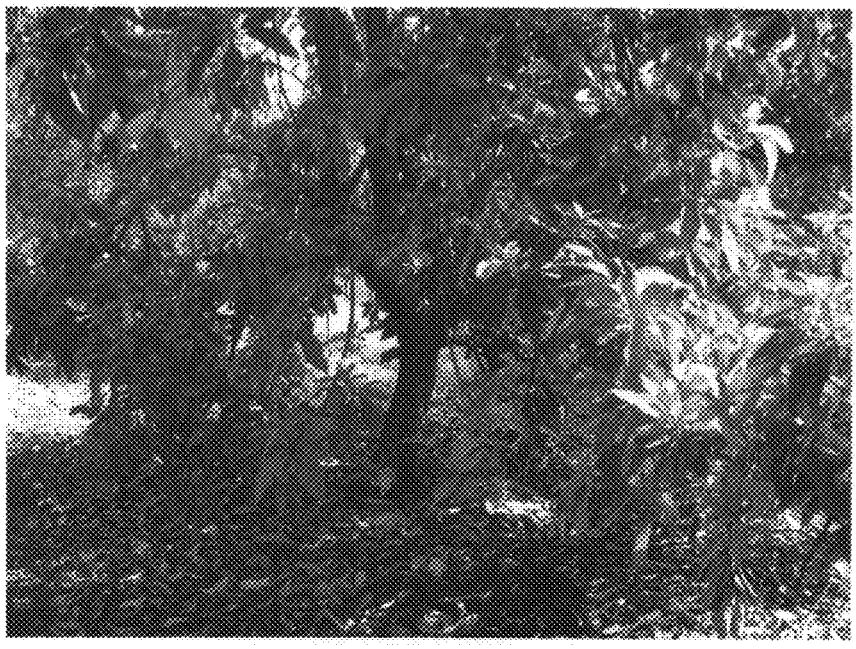
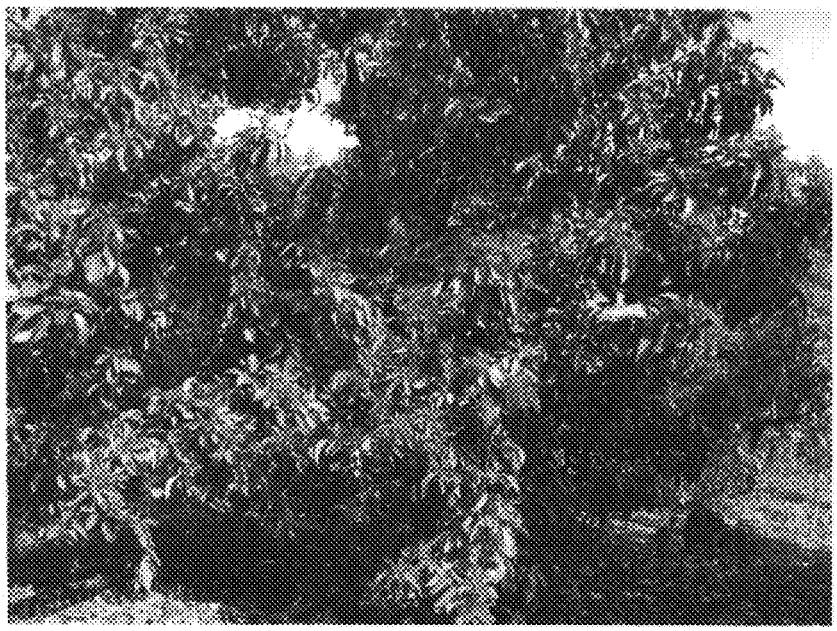
Fig. 2